(12) United States Patent
Cook et al.

(10) Patent No.: US 7,853,415 B2
(45) Date of Patent: Dec. 14, 2010

(54) MULTI-MEASUREMENT VORTEX FLOWMETER

(75) Inventors: Warren E. Cook, Upton, MA (US); Joseph J. Lewicke, Foxboro, MA (US); Peter E. Allstrom, Attleboro, MA (US); James H. Vignos, Needham Heights, MA (US)

(73) Assignee: Invensys Systems, Inc., Foxboro, MA (US)

( * ) Notice: Subject to any disclaimer, the term of this patent is extended or adjusted under 35 U.S.C. 154(b) by 521 days.

(21) Appl. No.: 11/680,975

(22) Filed: Mar. 1, 2007

(65) Prior Publication Data
US 2007/0150547 A1 Jun. 28, 2007

Related U.S. Application Data

(63) Continuation of application No. 10/235,835, filed on Sep. 6, 2002, now Pat. No. 7,212,928.

(51) Int. Cl.
*G01F 1/00* (2006.01)
(52) U.S. Cl. ........................................................ 702/45
(58) Field of Classification Search .................... 702/45
See application file for complete search history.

(56) References Cited

U.S. PATENT DOCUMENTS

| | | | |
|---|---|---|---|
| 3,948,098 A | 4/1976 | Richardson et al. | |
| 4,005,603 A | * 2/1977 | Golahny et al. | ........... 73/861.03 |
| 4,240,299 A | 12/1980 | Joy et al. | |
| 4,240,996 A | 12/1980 | Hunkar | |
| 4,331,912 A | 5/1982 | Ruesch et al. | |
| 4,448,081 A | 5/1984 | Kolitsch et al. | |
| 4,546,649 A | 10/1985 | Kantor | |
| 4,742,574 A | 5/1988 | Smith et al. | |
| 5,259,239 A | 11/1993 | Gaisford et al. | |
| 5,372,046 A | 12/1994 | Kleven et al. | |
| 5,429,001 A | 7/1995 | Kleven | |
| 5,497,329 A | 3/1996 | Tang | |
| 5,606,513 A | 2/1997 | Louwagie et al. | |
| 5,899,962 A | 5/1999 | Louwagie et al. | |
| 5,915,657 A | 6/1999 | Ptak | |
| 6,170,338 B1 | 1/2001 | Kleven et al. | |
| 6,386,046 B1 | 5/2002 | Mattar | |

(Continued)

OTHER PUBLICATIONS

Communication Pursuant To Article 96(2) EPC dated Jul. 27, 2007.

(Continued)

*Primary Examiner*—Aditya Bhat
(74) *Attorney, Agent, or Firm*—Fish & Richardson P.C.

(57) ABSTRACT

Two-wire transmitters are described in which the required voltage that a control room must supply to the transmitter is lower at high current than at low current, thus freeing up more voltage for other uses, and in which a constant set of operating voltages may be maintained. A corrected pressure in a vortex flow meter may be determined that reflects the mass flow rate. Thus, the mass flow rate may be determined based on the corrected pressure reading and a measured volumetric flow rate. Density may be determined from pressure and temperature using a table containing error values based on a standard density determination and a relatively simple approximation. During operation of a flow meter, the stored error values may be linearly interpolated and the approximation may be computed to determine the density from the stored error value.

21 Claims, 9 Drawing Sheets

U.S. PATENT DOCUMENTS

| | | | |
|---|---|---|---|
| 6,412,353 B1 | 7/2002 | Kleven et al. | |
| 6,484,590 B1 | 11/2002 | Kleven et al. | |
| 6,651,512 B1 | 11/2003 | Kleven et al. | |
| 6,658,945 B1 * | 12/2003 | Kleven | 73/861.22 |
| 6,721,610 B2 | 4/2004 | Gade et al. | |
| 6,732,595 B2 | 5/2004 | Lynnworth | |
| 2003/0114992 A1 * | 6/2003 | Morrow et al. | 702/23 |

OTHER PUBLICATIONS

Bernoulli Equation, http://hyperphysics.phy-astr.gsu.edu/hbase/pber.html, Sep. 3, 2002, pp. 1-6.

The Physics Classroom, Lesson 2: Sound Properties and Their Perception, http://www.glenbrook.k12.il.us/gbssci/phys/Class/sound/u1l12c.html, Aug. 30, 2002, pp. 1-8.

The Speed of Sound, http://www.mathpages.com/home/kmath109/kmath109.htm, Aug. 30, 2002, pp. 1-6

R.W. Miller, "Flow Measurement Engineering Handbook," $2^{nd}$ Edition (Copyright © 1989) (pp. 3-30 thru 3-33 and 6-32 thru 6-33).

R.W. Miller, "Flow Measurement Engineering Handbook," $3^{rd}$ Edition (Copyright © 1996) (pp. 3-23 thru 3-41 and 6-19 thru 6-51).

* cited by examiner

MULTI-MEASUREMENT VORTEX FLOWMETER

CROSS-REFERENCE TO RELATED APPLICATIONS

This application is a continuation of prior U.S. patent application Ser. No. 10/235,835, filed on Sep. 6, 2002. The disclosure of the prior application is considered part of (and is incorporated by reference in) the disclosure of this application.

TECHNICAL FIELD

Certain implementations relate generally to processing and transmitting data, and more particularly to power reduction and data processing in a vortex flow meter.

BACKGROUND

Flow meters may measure the rate of flow of a fluid in a pipe or other pathway. The fluid may be, for example, a gas or a liquid, and may be compressible or incompressible. One type of flow meter is a vortex flow meter which measures parameters including, for example, flow rate based on the principle of vortex shedding. Vortex shedding refers to a natural process in which a fluid passing a bluff body causes a boundary layer of slowly moving fluid to be formed along the surface of the bluff body. A low pressure area is created behind the bluff body and causes the boundary layer to roll up, which generates vortices in succession on opposite sides of the bluff body. The vortices induce pressure variations that may be sensed by a pressure sensor. The vortex-shedding pressure variations have a frequency that is related to the flow rate. Accordingly, by measuring the frequency of the pressure variations, the flow rate may be determined.

Vortex flow meters provide vortex frequency data that in conjunction with flow calibration factors determine the velocity and volumetric flow rate of the fluid passing through the meter. With inputted fluid density values, the mass flow rate can also be computed. These measurements, and others, can be transmitted to a control room or other receiver over a communication line, such as, for example, a standard two-wire 4-20 milliamp ("mA") transmission line.

SUMMARY

Certain implementations described below provide a two-wire transmitter in which the required voltage that a control room must supply to the transmitter is lower at high current than at low current, thus freeing up more voltage for other uses. The transmission line and any other resistive elements in the line generally consume more voltage at high current. Accordingly, the maximum load resistance of the transmission system, excluding the transmitter, is generally dictated by the transmitter's required voltage at high current. By lowering the transmitter's required voltage at high current, therefore, it is possible to design the rest of the system with a higher resistive load. The lower required voltage and the higher allowable load can be specified to a customer, allowing the customer to design a system to those specifications.

The required voltage can be lowered in these implementations because at high current the majority of the transmitter's current requirements can be met by doubling the current, rather than multiplying it by four. By merely doubling the current, the voltage is only divided by two, rather than by four. Thus, the required starting voltage, to achieve a given divided voltage, is also cut in half.

Certain implementations of a two-wire transmitter multiply the current by injecting the controlled current amplitude into either a first or a second of two current doublers coupled in series. If the current is low and needs to be multiplied by four, then the controlled current is injected into the first doubler. If, however, the current is high and only needs to be multiplied by two, then the controlled current is injected into the second doubler.

Certain of these implementations use a reverse power transformation for the first current doubler. In this way, when current is injected into the second current doubler, the current is also injected into the output of the first current doubler. The first current doubler then operates in reverse and divides the controlled current by two. The first current doubler, operating in reverse, also multiplies the voltage by two. Thus, even though the required voltage has been lowered, a higher voltage is still available to power circuitry needing the higher voltage. In this way, a constant set of operating voltages is maintained whether the received current is high or low.

Certain implementations of a transmitter described below determine a corrected pressure, based on a pressure reading and a velocity determination. The corrected pressure value along with a temperature measurement are used to determine the correct density value which in conjunction with the volumetric flow measurement allow the calculation of mass flow rate, for example.

Certain implementations calculate the density, using the corrected pressure and a measured temperature, by performing a table look-up of stored density errors. The stored density errors are linearly interpolated to provide a density error corresponding to the desired pressure and temperature. The interpolated density error reflects an estimate of an error between a standard density value and an approximated density. The approximated density is computed for the desired pressure and temperature, and combined with the interpolated density error to yield the estimate of the actual density value. In this way, instead of computing the actual density value in real time, the approximated density is computed in real time. Because the actual density calculation is generally a time consuming calculation, and because the density approximation can be selected to be comparatively fast, the estimate of the density is determined quickly in real time.

According to a general aspect, specifying a transmitter for regulating an amplitude of a supplied current to encode a parameter includes providing a set of data to a customer. The set of data represents a maximum allowable load at one or more supply voltage levels. The set of data has a first segment used only for a lower range of currents below a transition current, and a second segment used only for a higher range of currents above the transition current.

The first segment may result from the transmitter multiplying a regulated current by a first non-unitary factor when the regulated current is within the lower range of currents. The second segment may result from the transmitter multiplying the regulated current by a second non-unitary factor when the regulated current is within the higher range of currents. The first segment may approximate a first line having a first slope. The second segment may approximate a second line having a second slope. The first slope may be at least twice as large as the second slope.

According to another general aspect, controlling a current signal includes receiving a current with a variable amplitude over a line, wherein the amplitude is regulated. The regulated amplitude is multiplied by a first non-unitary factor when the regulated amplitude is below a first level. The regulated amplitude is multiplied by a second non-unitary factor when the regulated amplitude is above a second level. A constant set of operating voltages is maintained whether the regulated amplitude is multiplied by the first non-unitary factor or the second non-unitary factor. The multiplied amplitude and the constant set of operating voltages are provided to circuitry.

Receiving the variable current may include receiving the current at a transmitter. The amplitude may be regulated by the transmitter to communicate an output parameter by encoding a value of the output parameter on the current. Maintaining a constant set of operating voltages may include using a reversible power transformation. Multiplying by the first non-unitary factor may include injecting the regulated current into an input of a first multiplier and coupling an output of the first multiplier to an input of a second multiplier. Multiplying the second non-unitary factor may include injecting the regulated current into the input of the second multiplier and into the output of the first multiplier. Maintaining the constant set of operating voltages may include using a reversible multiplier for the first multiplier, allowing regulated current that is coupled to the output of the first multiplier to produce a current emanating from the input to the first multiplier and having an amplitude approximately equal to the regulated current divided by the first non-unitary factor. Maintaining the constant set of operating voltages may further include regulating a voltage at the input of the first multiplier, providing the same voltage whether the regulated current is injected into the input of the first multiplier or the input of the second multiplier.

The transmitter may receive power from a supply over the line. The regulated current may extend over a range of about 4 milliamps to 20 milliamps. The output parameter may be a vortex frequency, a linear flow rate, or a volumetric flow rate. Receiving the variable current may include receiving the current at a transmitter, and the amplitude may be regulated before being received by the transmitter.

According to another general aspect, a transmitter includes a switching circuit configured to couple a regulated current to either a first output or a second output based on the amplitude of the regulated current. The transmitter includes a first non-unitary current multiplier having an input and an output, with the input of the first non-unitary multiplier being coupled to the first output of the switching circuit, wherein the first non-unitary multiplier is configured to operate in a forward direction as a current multiplier and in a backward direction as a current divider. The transmitter includes a second non-unitary multiplier having an input and a output, with the input of the second non-unitary multiplier being coupled to both the second output of the switching circuit and the output of the first non-unitary multiplier.

The transmitter may include a current regulator coupled to an input of the switching circuit and configured to regulate an amplitude of the current to encode a value of an output parameter on the current. The current regulator may be configured to receive the current over a line in a two-wire system. The current regulator may be configured to regulate the amplitude over a range extending at least from 4 milliamps to 20 milliamps. The current regulator may be configured as part of a vortex flow meter system and be configured to encode a value of a vortex frequency, a linear flow rate, or a volumetric flow rate.

According to another general aspect, a transmitter includes a switching mechanism having a first output and a second output, for coupling a regulated current to either the first output or the second output based on the amplitude of the regulated current. The transmitter includes a first mechanism for multiplying current by a non-unitary number, the first mechanism having an input and an output, with the input of the first mechanism being coupled to the first output of the switching mechanism, wherein the first mechanism is configured to operate in a forward direction as a current multiplier and in a backward direction as a current divider. The transmitter includes a second mechanism for multiplying current by a non-unitary number, the second mechanism having an input and an output, with the input of the second mechanism being coupled to both the second output of the switching mechanism and the output of the first mechanism.

The transmitter may further include a regulating mechanism coupled to the switching mechanism for regulating the amplitude of the current to encode a value of an output parameter on the current.

According to another general aspect, determining a pressure includes (i) measuring a pressure of a fluid flowing through a system, (ii) measuring a temperature of the flowing fluid, (iii) determining a velocity of the flowing fluid, and (iv) determining a corrected pressure for the flowing fluid based on the pressure, the temperature, and the velocity, wherein the corrected pressure corresponds to a density reflective of the velocity and a mass flow rate.

Determining a pressure may include determining a density based on the pressure and the temperature, and determining the corrected pressure may include using the following formula:

$$P_c \cong P_{ps} + \frac{1}{2} \times k_{\mathit{diff}} \times \rho_{ps} \times V_{VOR}^2.$$

The constant $k_{\mathit{diff}}$ may be determined during a calibration procedure for a portion of the system, during which the mass flow rate is known. The calibration procedure may include (i) measuring a calibration pressure, (ii) measuring a calibration temperature, (iii) determining a calibration density based on the calibration pressure and the calibration temperature, (iv) determining a calibration velocity, (v) determining a calibration volumetric flow rate, (vi) determining the corrected pressure using the known mass flow rate, the calibration temperature, and the calibration volumetric flow rate, and (vii) determining the constant $k_{\mathit{diff}}$ by using the following formula:

$$k_{\mathit{diff}} = \frac{2 \times (P_c - P_{ps})}{\rho_{ps} \times V_{VOR}^2}.$$

The calibration procedure may include (i) measuring a calibration pressure, (ii) measuring a calibration temperature, (iii) determining a calibration density based on the calibration pressure and the calibration temperature, (iv) determining a calibration velocity, (v) determining a volumetric flow-rate, and (vi) determining the constant $k_{\mathit{diff}}$ by using the following formula:

$$k_{\mathit{diff}} = 2 \times \left(\frac{c}{V_{VOR}}\right)^2 \times \left(\frac{Q_m}{\rho_{ps} \times Q_v} - 1\right).$$

Determining a pressure may further include (i) determining a volumetric flow rate from the velocity, (ii) determining the density, and (iii) determining a mass flow rate from the volumetric flow rate and the density. Determining the velocity may include using a vortex flow meter to determine a vortex frequency, and determining the velocity based on the vortex frequency.

A device may include a storage medium having instructions stored thereon that when executed result in at least the following: (i) measuring a pressure of a fluid flowing through a system, (ii) measuring a temperature of the flowing fluid, (iii) determining a velocity of the flowing fluid, and (iv) determining a corrected pressure for the flowing fluid based on the pressure, the temperature, and the velocity, the corrected pressure corresponding to a density reflective of the velocity and a mass flow rate. The device may further include a controller that is part of a transmitter in a vortex flow meter system, the controller being operable to execute the instructions. The device may include a compact diskette.

According to another general aspect, calibrating a device includes (i) measuring a pressure of a fluid flowing in a system, (ii) measuring a temperature of the flowing fluid, (iii) determining a density of the flowing fluid based on the pressure and the temperature, (iv) determining a velocity of the flowing fluid, (v) determining a volumetric flow rate of the flowing fluid, (vi) determining a corrected pressure using a mass flow rate, the determined volumetric flow rate, and the measured temperature, wherein the corrected pressure corresponds to a corrected density reflective of the determined velocity and the mass flow rate, and (vii) determining a calibration constant $k_{diff}$ according to the following equation:

$$k_{diff} = \frac{2 \times (P_c - P_{ps})}{\rho_{ps} \times V_{VOR}^2}.$$

The calibration constant $k_{diff}$ may be used to determine another corrected pressure during operation with a second mass flow rate according to the following equation:

$$P_c \cong P_{ps} + \frac{1}{2} \times k_{diff} \times \rho_{ps} \times V_{VOR}^2.$$

The device may include a vortex flow meter, the vortex flow meter may be used to measure a vortex frequency of the flowing fluid, and the velocity may be determined based on the measured vortex frequency.

A device may include a storage medium having instructions stored thereon that when executed result in at least the following: (i) measuring a pressure of a fluid flowing in a system, (ii) measuring a temperature of the flowing fluid, (iii) determining a density of the flowing fluid based on the pressure and the temperature, (iv) determining a velocity of the flowing fluid, (v) determining a volumetric flow rate of the flowing fluid, (vi) determining a corrected pressure using a mass flow rate, the determined volumetric flow rate, and the measured temperature, wherein the corrected pressure corresponds to a corrected density reflective of the determined velocity and the mass flow rate, and (vii) determining a calibration constant $k_{diff}$ according to the following equation:

$$k_{diff} = \frac{2 \times (P_c - P_{ps})}{\rho_{ps} \times V_{VOR}^2}.$$

The device may include a controller that is part of a transmitter in a vortex flow meter system, the controller being operable to execute the instructions.

According to another general aspect, calibrating a device includes (i) measuring a pressure of a fluid flowing in a system, (ii) measuring a temperature of the flowing fluid, (iii) determining a density of the flowing fluid based on the pressure and the temperature, (iv) determining a velocity of the flowing fluid, (v) determining a volumetric flow rate of the flowing fluid, and (vi) determining a calibration constant, using a known speed of sound in the flowing fluid and a mass flow rate, according to the following equation:

$$k_{diff} = 2 \times \left(\frac{c}{V_{VOR}}\right)^2 \times \left(\frac{Q_m}{\rho_{ps} \times Q_v} - 1\right).$$

The calibration constant $k_{diff}$ may be used to determine a corrected pressure during operation with a second mass flow rate according to the following equation:

$$P_c \cong P_{ps} + \frac{1}{2} \times k_{diff} \times \rho_{ps} \times V_{VOR}^2,$$

and the corrected pressure may correspond to a corrected density reflective of the determined velocity and the second mass flow rate. The device may include a vortex flow meter, calibrating the device may further include using the vortex flow meter to measure a vortex frequency of the flowing fluid, and the velocity and the volumetric flow rate of the flowing fluid may be determined based on the vortex frequency.

A device may include a storage medium having instructions stored thereon that when executed result in at least the following: (i) measuring a pressure of a fluid flowing in a system, (ii) measuring a temperature of the flowing fluid, (iii) determining a density of the flowing fluid based on the pressure and the temperature, (iv) determining a velocity of the flowing fluid, (v) determining a volumetric flow rate of the flowing fluid, and (vi) determining a calibration constant, using a known speed of sound in the flowing fluid and a mass flow rate, according to the following equation:

$$k_{diff} = 2 \times \left(\frac{c}{V_{VOR}}\right)^2 \times \left(\frac{Q_m}{\rho_{ps} \times Q_v} - 1\right).$$

The device may further include a controller that is part of a transmitter in a vortex flow meter system, the controller being operable to execute the instructions.

According to another general aspect, computing density includes (i) accessing a pressure input and a temperature input, (ii) determining a density error for the pressure input and temperature input based on one or more stored density errors, wherein the one or more stored density errors each reflect error between a density approximation and a standard density value for a different pressure input and temperature input, (iii) determining a density approximation for the pressure input and temperature input, and (iv) determining a density value for the pressure input and temperature input based on the density error for the pressure input and temperature input and the density approximation for the pressure input and temperature input.

Determining the density error for the pressure input and temperature input may include interpolating between at least two stored density errors. Interpolating may include linear interpolating. The one or more stored density errors may include multiple stored density errors and the multiple stored density errors may represent density errors for different pressure and temperature inputs that are not equally spaced in at least one of pressure or temperature. The spacing of at least one of pressure and temperature may be closer for a first pressure and temperature range than for a second pressure and temperature range, and density may change more rapidly within the first range than the second range.

The one or more stored density errors may include multiple stored density errors and the multiple stored density errors may each have been scaled. Error between a given density approximation and a given standard density value may be expressed as a ratio involving the given density approximation and the given standard density value. The one or more stored density errors may include stored density errors for pressure and temperature inputs on both a first side and a second side of a saturation line, and stored density errors for pressure and temperature inputs on the second side may be based on an extrapolation of standard density values for pressure and temperature inputs on the first side.

Determining the density approximation for the pressure input and temperature input may include using an approximation equation that is a third order, or lower order, equation, and an error between the determined density value and a standard density value for the pressure input and temperature input may be 0.1% or less. Determining the density approximation for the pressure input and temperature input may include using a virial equation. Determining the density approximation for the pressure input and temperature input may include using an approximation equation that has been tailored to a range of densities needed. The approximation equation may include a virial equation having coefficients that have been tailored to the range of densities needed.

A device may include a storage medium having instructions stored thereon that when executed result in at least the following: (i) accessing a pressure input and a temperature input, (ii) determining a density error for the pressure input and temperature input based on one or more stored density errors, wherein the one or more stored density errors each reflect error between a density approximation and a standard density value for a different pressure input and temperature input, (iii) determining a density approximation for the pressure input and temperature input, and (iv) determining a density value for the pressure input and temperature input based on the density error for the pressure input and temperature input and the density approximation for the pressure input and temperature input. The device may further include a controller that is part of a transmitter in a vortex flow meter, the controller being operable to execute the instructions.

According to another general aspect, a device includes a storage medium having stored thereon density errors computed using at least the following operations: (i) determine a standard density value for each of multiple pressure and temperature input pairs, (ii) determine a density approximation for each of the multiple pressure and temperature input pairs, and (iii) determine a density error, based on the standard density value and the density approximation, for each of the multiple pressure and temperature input pairs.

The multiple pressure and temperature input pairs need not be equally spaced in at least one of pressure or temperature. The spacing of at least one of pressure and temperature may be closer for a first pressure and temperature range than for a second pressure and temperature range, and density may change more rapidly within the first range than the second range. The multiple determined density errors may be scaled before being stored on the storage medium. Determining the density error for each of the multiple pressure and temperature input pairs may include determining a ratio involving the standard density value and the density approximation for each of the pressure and temperature input pairs.

The multiple pressure and temperature input pairs may include pairs on both a first side and a second side of a saturation line, and determining a standard density value for pressure and temperature input pairs on the second side may be based on an extrapolation of standard density values for pressure and temperature input pairs on the first side. Determining the density approximation for each of the multiple pressure and temperature input pairs may include using an approximation equation that is a third order, or lower order, equation.

Determining the density approximation for each of the multiple pressure and temperature input pairs may include using a virial equation. Determining the density approximation for each of the multiple pressure and temperature input pairs may include using an approximation equation that has been tailored to a range of the determined standard density values. Determining the density approximation for each of the multiple pressure and temperature input pairs may include using a virial equation having coefficients that have been tailored to the range of the determined standard density values.

The details of one or more implementations are set forth in the accompanying drawings and the description below. Other features will be apparent from the description, the drawings, and the claims.

DETAILED DESCRIPTION

General Description and Power Control

Figure 1:
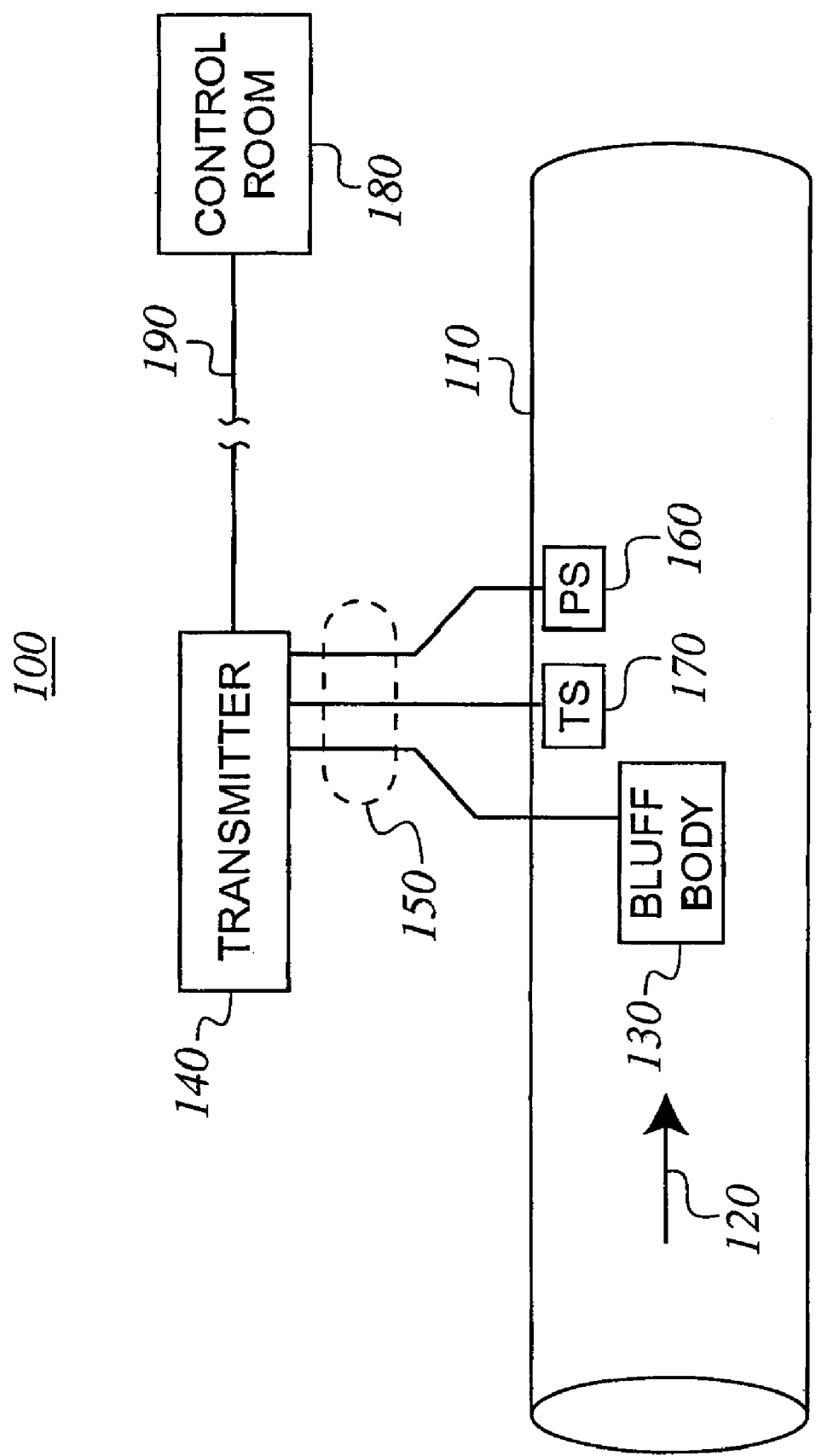
FIG. 1 shows one implementation of a system including a vortex flow meter.

Referring to FIG. 1, a system 100 includes a pipe 110 through which a fluid is flowing in the direction indicated by an arrow 120. Fluid flows past a bluff body 130 that generates vortices in succession on opposite sides of the bluff body 130. The vortices induce pressure variations that are sensed by a vortex pressure sensor (not shown) and converted to an electrical signal that is provided to a transmitter 140 over a set of communication lines 150. The transmitter 140 also receives signals over the communication lines 150 from a pressure sensor 160 and a temperature sensor 170 that measure the pressure and temperature, respectively, of the fluid away from the bluff body 130 vortices. The transmitter 140 is coupled to a control room 180 over a two-wire transmission line 190. The control room 180 provides power to the transmitter 140 over the line 190 by providing current at a specific voltage. The amount of current supplied is controlled by the transmitter 140 and is used to communicate the value of an output parameter. The output parameter may be, for example, fluid velocity, volumetric flow rate, or mass flow rate. In the case where the line 190 is part of a 4-20 mA transmission system, the transmitter varies the current between approximately 4 mA and 20 mA depending on the level of the output parameter. In practice, 4-20 mA systems have an actual current that may fluctuate between, for example, 3.6 mA and 22 mA.

Figure 2:
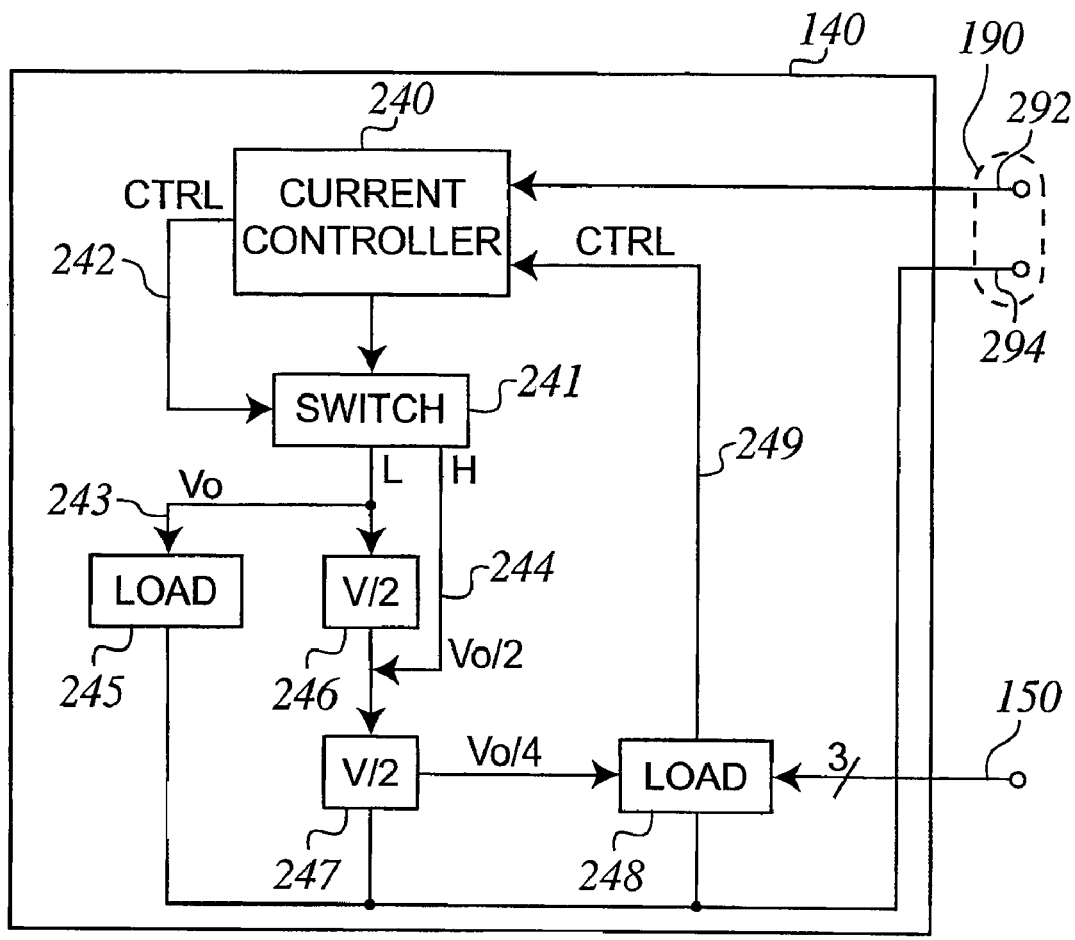
FIG. 2 shows an exemplary implementation of the transmitter from FIG. 1.

Referring to FIG. 2, the transmitter 140 receives power over an input line 292. The input power has a voltage determined by the control room 180 and is received by a current controller 240. The current controller 240 determines the amount of current that is drawn by the transmitter 140 and supplies the current to a switch 241. The current controller 240 controls the switch 241 using a control line 242. If the current is low, then the control line 242 directs the switch 241 to inject the current out of an output 243 (labeled "L") that is shunt regulated at $V_O$ volts. If the current is high, then the control line 242 directs the switch 241 to inject the current out of an output 244 (labeled "H") that is shunt regulated at $V_O/2$ volts.

The output 243 is coupled to a load 245 and a voltage divider 246. The load 245 represents circuitry operating at a voltage of $V_O$ volts. The voltage divider 246 is a divide-by-two circuit, and also has the effect of doubling the current. Thus the voltage divider 246 can equivalently be referred to as a current multiplier. The voltage divider 246 is also a reversible power transformer, meaning that it can be operated in the reverse direction as explained below.

The output 244 is coupled to a voltage divider 247 that divides the voltage by two and multiplies the current by two, providing the output signal to a load 248. The load 248 represents circuitry operating at $V_O/4$ volts. In one implementation having $V_O$ set to 14 volts, $V_O/4$ is 3.5 volts and most of the circuitry for processing the fluid flow information operates at $V_O/4$. The load 248 receives the communication lines 150 that include signals representing the vortex pressure signal as well as the pressure and temperature at a point away from the vortices. The load 248 supplies a control signal 249 to the current controller 240 indicating how much current the transmitter 140 should draw to properly encode the output parameter. The indication may be, for example, the level of the output parameter or the level of the current that should be drawn.

The output 244 is also coupled to the "output" of the voltage divider 246. Because the voltage divider 246 is reversible, the controlled current is divided by two (and the voltage is doubled) by the voltage divider operating in reverse, and the resulting signal appears at the output 243 of the switch 241. Using a reversible power transformation, such as the voltage divider 246, allows the transmitter 140 to maintain a constant set of operating voltages irrespective of whether a low current or a high current is being drawn. Although the operating voltages are maintained, the amount of current at each of those voltages varies.

Figure 3:
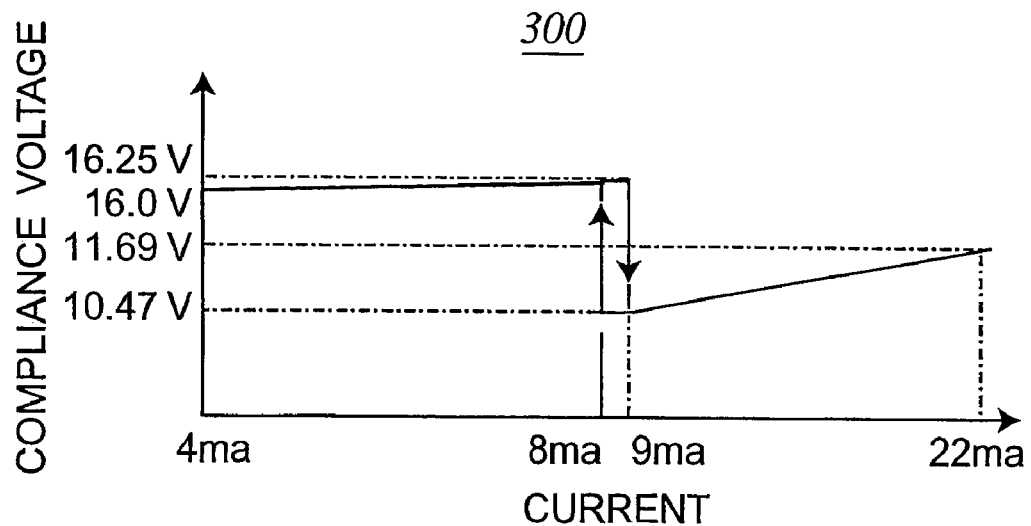
FIG. 3 is a graph of compliance voltage versus current for the transmitter of FIG. 2.

Referring to FIG. 3, a graph 300 shows compliance voltage versus current for the transmitter 140, where compliance voltage is the voltage required by the transmitter. As the graph 300 indicates, at high current the required voltage is lower than at low current. The discussion of FIG. 2 above stated that the switch 241 provided current on the output 243 for low current and on the output 244 for high current. As the graph 300 suggests, "low" generally refers to current below 8 mA and "high" generally refers to current above 9 mA. The graph 300 also shows that hysteresis is built into the current controller 240 so that it does not oscillate around a switch point.

At low current, the circuitry of one implementation of the transmitter 140 requires 15.8 volts plus the voltage drop across a 50 Ohm load. At 4 ma, the voltage drop across 50 Ohms is 0.20 volts and the total required voltage is 16.0 volts, as indicated in the graph 300. At 9 ma, the voltage drop across 50 Ohms is 0.45 volts and the total required voltage is 16.25 volts, as indicated in the graph 300. These voltages reflect a shunt regulated $V_O$ equal to 13.75 volts. After 9 ma, as indicated in FIG. 2, the controlled current is injected at a voltage of $V_O/2$, which is 6.875 volts. The required voltage does not drop by $V_O/2$ due to the presence of additional circuitry (not shown in FIG. 2), but the required voltage does drop to 9.625 volts (a drop of 6.175 volts) plus the voltage drop across a 94 Ohm load which reflects an additional 44 Ohm resistor (not shown in FIG. 2). At 9 ma, the voltage drop across 94 Ohms is 0.846 volts and the total required voltage is 10.47 volts. At 22 ma, the voltage drop across 94 Ohms is 2.068 volts and the total required voltage is 11.69 volts.

Figure 4:
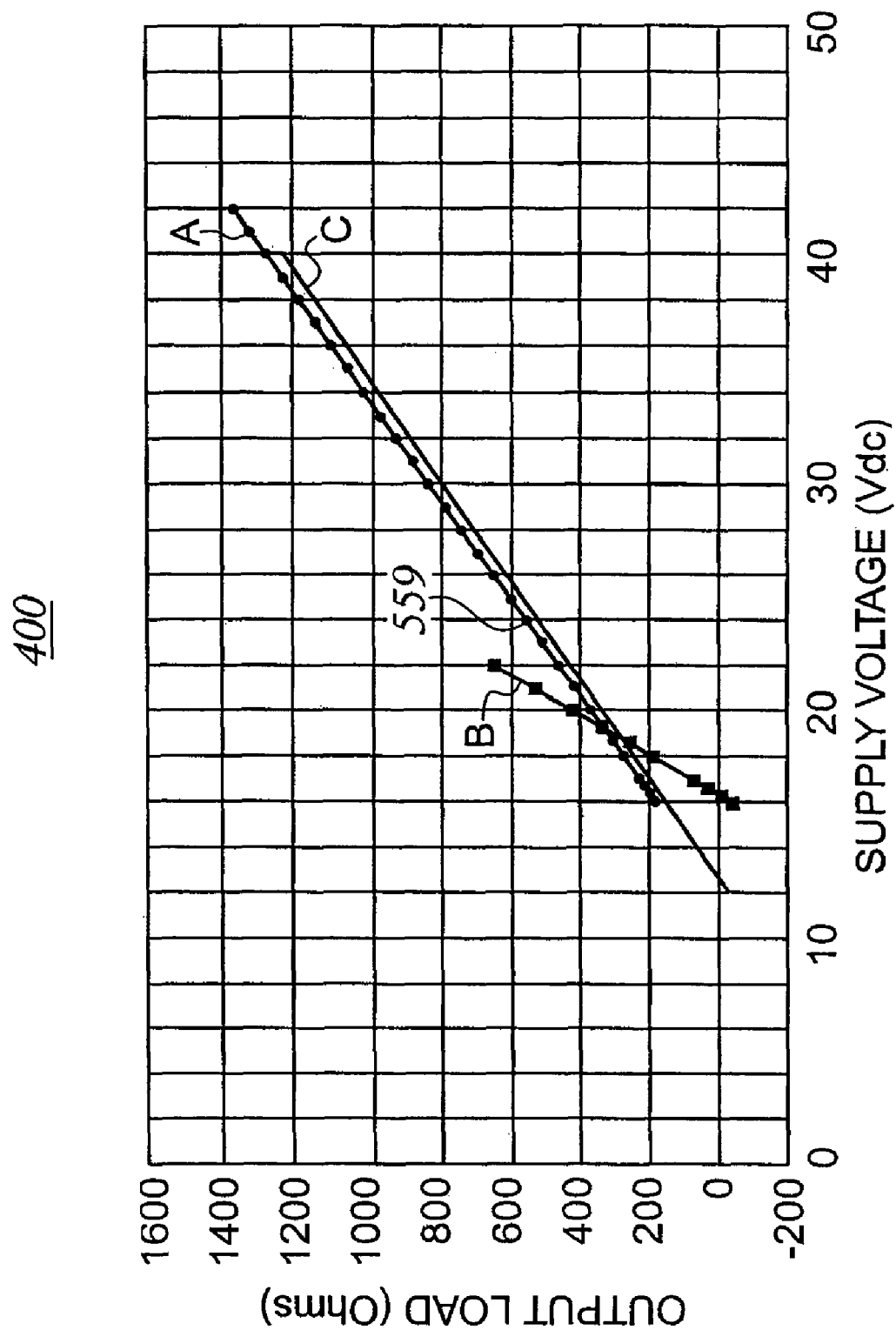
FIG. 4 is a graph of output load versus supply voltage for the transmitter of FIG. 2.

Referring to FIG. 4, a graph 400 shows the impact on allowed load from reducing the required voltage at high current. The voltage supplied by the control room 180, shown on the x-axis of the graph 400, is expended in the various components of a transmission loop. Those components may include, for example, the transmitter 140, the transmission line 190, various other components including a sense resistor used by the control room 180 to sense the current, and an intrinsic safety ("IS") barrier having a resistance. A system designer is generally interested in knowing the maximum output load that can be used with a given transmitter. That information can be supplied by the graph 400 for the transmitter 140. For example, a line A shows that with a 24 volt power supply, the transmission loop can have an output load of 559 Ohms. If a sense resistor having 250 Ohms is used, and IS barrier resistance is 273 Ohms, then 36 Ohms is available for line drop. Using 24 American Wire Gauge ("AWG") wire, 36 Ohms allows for a loop of 697 feet each way, for a round trip of 2*697 feet.

The line A reflects the output load allowable when the transmitter is drawing a high current. The data points in the line A assume that 22 mA is being drawn, which leaves the least amount of voltage remaining for the rest of the transmission system. Because the required voltage at 22 mA is 11.69 volts ("V"), there is approximately 12.3 V (24-11.69) available. This allows a resistance of 559 Ohms (12.3 V/22 mA). A line B reflects the output load allowable when the transmitter is drawing a low current. The data points in the line B assume that 9 mA is being drawn, because that is the highest "low" current. Thus, data points on the line B have a resistance of (supply voltage—16.25 V)/9 mA. If the line B were shown for 24 V, it would provide an allowable resistance of 861 Ohms (7.75 V/9 mA). As indicated in the preceding examples, the data points on each of the lines A and B assume that all supplied voltage except for the required compliance voltage is available and Ohm's Law ($V=I*R$) is used to determine the allowable output load at the maximum current. The maximum output load allowable for a system is the lower of the two values provided by the lines A and B for a given voltage supply. By lowering the required voltage at high currents, the transmitter 140 is making additional power available to the rest of the system when the system needs it most.

A line C reflects the output load line for a transmitter with a compliance voltage of approximately 12.5 volts, for all current values. As can be seen, the implementation of the lines A and B, having a variable compliance voltage, allows a higher load resistance than the implementation of the line C for all supply voltages higher than approximately 19 V. The implementation of the lines A and B draws a power equal to (4 mA)*(16.25 V), or 65 milliwatts. The implementation of the line C, however, draws only (4 mA)*(12.5 V), or 50 milliwatts. Thus, for supply voltages of 19 V or more, the implementation of the lines A and B draws 30% more power than the implementation of the line C and allows a load that is at least as large.

The allowable output load can be increased by moving the switching point and by lowering the required voltage at either high or low current. For example, if the switching point were lowered from 9 mA to a lower value, then the line B would maintain the same allowable resistance of zero Ohms at approximately 16.25 volts, but would rotate counterclockwise about that point (slope is 1/I). When the injection point is moved and the switching point is lowered, the minimum required power needs to be maintained. Thus, in the implementation of FIG. 2, when the injection point is moved to the junction between the voltage dividers 246, 247, the switching point is not lowered below 8 mA and the minimum required power is maintained. For example, power of at least $V_o$ volts*4 mA is maintained at the output 243 of the switch 241 regardless of the value of the regulated current. Additionally, if the required voltage at high current (or low current) were lowered, then the line A (or the line B) would shift to the left.

As explained earlier, the implementation of FIGS. 2-4 uses two current multipliers (voltage dividers) 246, 247. The use of two non-unitary multipliers (that is, multipliers that multiply by a number other one) to achieve the desired low-current multiplication allows one of the multipliers (the voltage divider 246) to be switched out at high-current while the other multiplier (the voltage divider 247) remains in the circuit. Switching out only one of the voltage dividers allows the switching point to be lower than if all of the voltage dividers were switched out, as further explained below with respect to FIG. 5. This results in a steeper low-current line segment in a corresponding load curve, and allows more load points to be characterized by the high-current line, which also shifts left by a lower amount because of the lower transition point.

Figure 5:
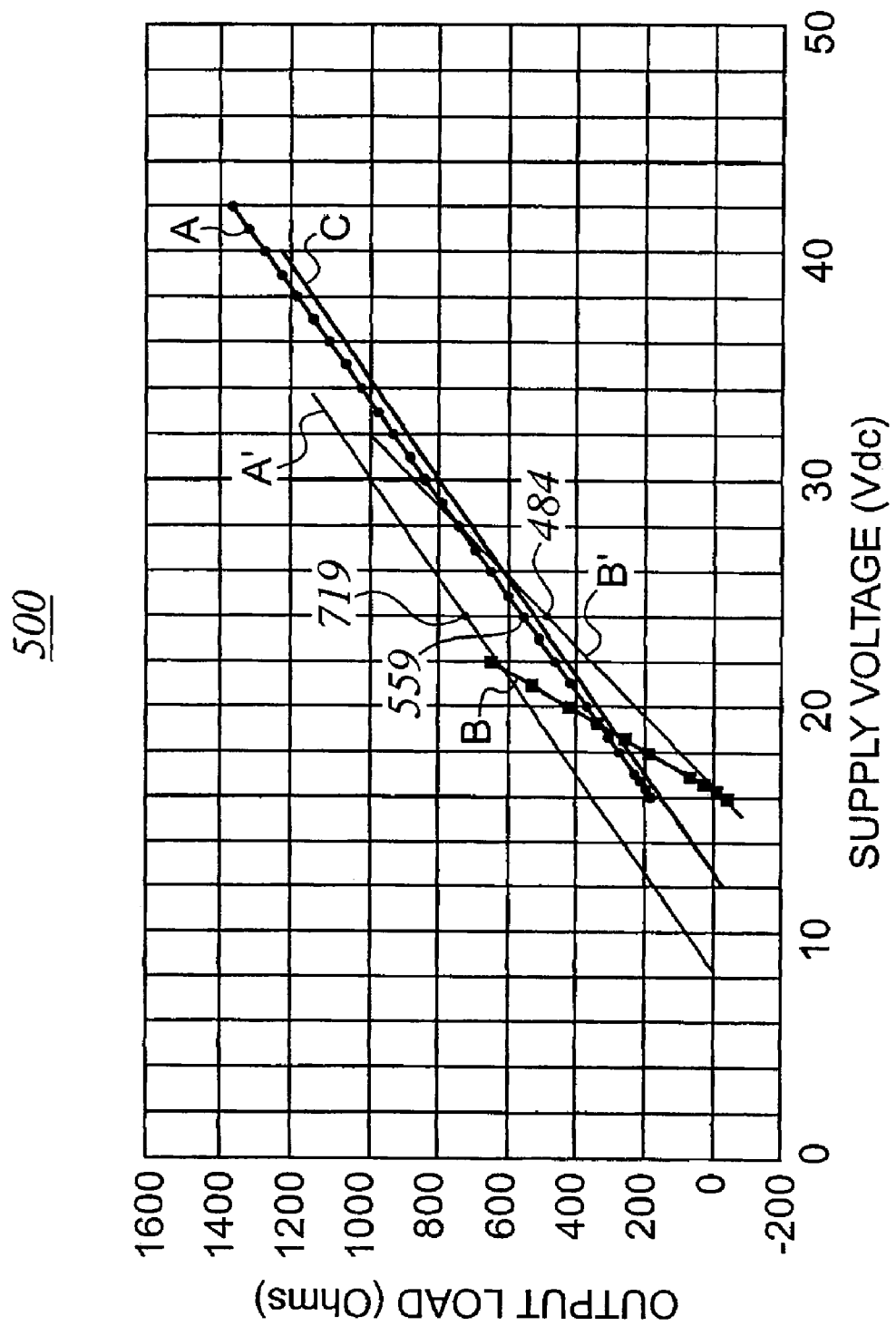
FIG. 5 is a graph of output load versus supply voltage for another implementation of a transmitter.

Referring to FIG. 5 for an example, if the implementation of FIG. 2 is modified so that the two voltage dividers 246, 247 are combined into a divide-by-four, then the switching point would not be until approximately 16 mA (ignoring any hysteresis), instead of 8 mA. This is because at least 16 mA are provided to the load 248. That would result in a low-current load curve having a line B' (corresponding to the line B) with a slope of 1/0.016, rather than 1/0.009. Additionally, because both voltage dividers are switched out at 16 mA in this example, the required high-current voltage would further drop by approximately $V_o/4$ (approximately 3.5 volts), resulting in a line A' (corresponding to the line A) shifted left by an additional 3.5 volts. A customer with a supply voltage of 24 volts would now only be allowed to insert approximately 484 Ohms into the transmission loop. Note that 484 Ohms is given by the line B' (24-16.25 V/16 mA) rather than the line A' which yields approximately 719 Ohms (24-(11.69-3.5) V/22 mA). The new load figure of 484 Ohms is less than that provided by the implementation of FIG. 2 which is 559 Ohms.

An examination of the slopes of the various lines is instructive. The line A has a slope of approximately 45.5 (1/0.022), whereas the line B has a slope of approximately 111.1 (1/0.009), which is more than twice that of the line A. The line A' also has a slope of approximately 45, but the line B' has a slope of only approximately 62.5 (1/0.016).

Implementations of the transmitter 140 may switch at different current values and at multiple current values. Different schemes may be used to divide or multiply the voltage or current, including, for example, a divide-by-three circuit. More than one divider/multiplier may be reversible and different sets of operating voltages may be used. Further, the set of operating voltages need not be maintained for all current values. Different transmission schemes may also be used, such as, for example, a three-wire system with separate power and signal lines and a common ground. Even if appreciable operating power is not being drawn off of the same line on which the signal is encoded, implementations of the transmitter 140 can be used to lower the power consumed by a transmitter off of the signal line, thereby allowing the control room to be designed to provide a signal line having less power and improving the transmitter's cooling requirements. Implementations of the transmitter 140 are not restricted to vortex meter applications or to metering applications generally, and may be used in other applications in which a parameter is being communicated between two points.

Data Processing

Referring again to FIG. 2, implementations of the load 248, or some other component, may be used to process fluid data in a variety of ways. One processing task common in vortex flow meters is to convert the vortex pressure signal into a vortex frequency and then to determine the velocity and/or the volumetric flow rate from the vortex frequency. The relationship between a vortex frequency and fluid velocity is linear. A factor may be computed using calibration procedures for each flow meter. The factor is a constant that relates vortex shedding frequency to volumetric flow rate for the specific flow meter.

Another processing task involves converting a volumetric flow rate into a mass flow rate. Mass flow rate is equal to the product of volumetric flow rate multiplied by density. For compressible fluids, the density can vary considerably from point to point in the flow meter. It is desirable to determine an appropriate pressure value, referred to as a corrected pressure, that leads to a density that can be multiplied by the measured volumetric flow rate (determined by a vortex flow meter or otherwise) to yield the correct mass flow rate. Because temperature can be taken to be constant throughout the flow meter in certain implementations, density can be determined from pressure and temperature using the standard relation of density=(universal gas constant)*(temperature)/(pressure).

By analyzing collected data it has been determined that the pressure measured downstream of a bluff body, relative to the pressure at the input to a flow meter, can be given by equation 1 below:

$$P_{ps} \cong P_o - \frac{1}{2} \times k_{ps} \times \rho_{ps} \times V_{VOR}^2 \qquad (1)$$

where, $P_{ps}$=pressure measured at the pressure sensor location, $P_o$=reference pressure at the input to the flow meter, $k_{ps}$=constant related to location of the pressure sensor, $\rho_{ps}$=density determined at the measured pressure and temperature, and $V_{VOR}$=flow velocity calculated from the vortex shedding frequency.

It has further been determined that the corrected pressure can be given by equation 2 below:

$$P_c \cong P_o - \frac{1}{2} \times k_c \times \rho_{ps} \times V_{VOR}^2 \quad (2)$$

where, $P_c$=corrected pressure as defined above, and
$k_c$=constant related to the unknown location of the corrected pressure.

Subtracting equation (1) from equation (2) yields equation 3 below for the corrected pressure:

$$P_c \cong P_{ps} + \frac{1}{2} \times k_{diff} \times \rho_{ps} \times V_{VOR}^2 \quad (3)$$

where, $k_{diff} \equiv k_{ps} - k_c$, $V_{VOR} = \frac{4 \times f_{VOR}}{\pi \times d^2 \times K_{COR}}$, $f_{VOR}$=vortex frequency,
$K_{COR}$=constant relating $f_{VOR}$ to $Q_V$ (volumetric flow rate), corrected for conditions such as temperature, upstream effects, and the thickness of mating pipe, and
d=diameter of flow meter at bluff body.

The term $k_{diff}$ is a constant for a given flow meter line size, and can be determined by a mass flow calibration without having to determine the term $k_c$. Two procedures are now described, both of which include measuring or otherwise determining the mass flow rate through the flow meter.

Figure 6:
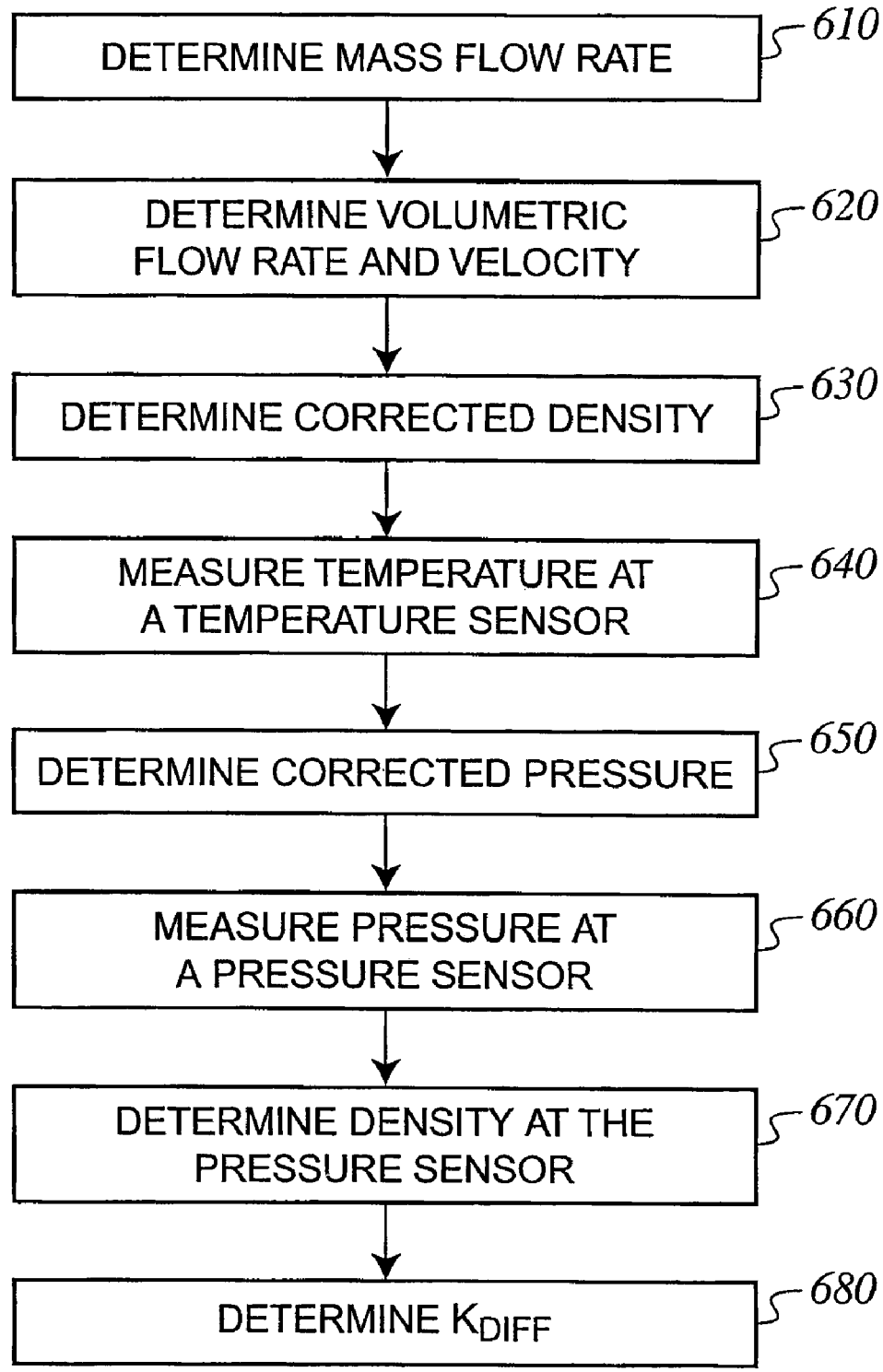
FIG. 6 shows a first calibration process to determine the term $k_{diff}$.

Referring to FIG. 6, a first calibration process 600 determines $k_{diff}$ by solving equation 3 for $k_{diff}$ and determining a calibration value for the corrected pressure. The process 600 includes determining the mass flow rate of the fluid through the flow meter (610). This may be done, for example, at a calibration facility that monitors or controls the mass flow. With the mass flow rate of the standard (calibration facility) being known, and the vortex volumetric flow rate and fluid temperature being known, the factor by which the measured pressure must be adjusted to compute the density and corresponding mass flow rate can be determined. This factor is $k_{diff}$ and will be a constant for each line size vortex flow meter due to the fact that the measured pressure value is taken at a precise position in the flow tube.

The process 600 includes determining the volumetric flow rate and the velocity (620). In a vortex flow meter implementation, the volumetric flow rate may be determined by, for example, determining the vortex frequency and multiplying that frequency by $K_{COR}$. The velocity can be determined, for example, from the volumetric flow rate by dividing by the cross-sectional area of the flow.

The process 600 includes determining the corrected density (630). This may be done, for example, by dividing the mass flow rate by the volumetric flow rate, as shown in the following equation 4:

$$\rho_c = \frac{Q_m}{Q_v} = \frac{Q_m \times K_{COR}}{f_{VOR}} \quad (4)$$

As equation 4 shows, the volumetric flow rate need not be determined explicitly in operation 620, because the vortex frequency and $K_{COR}$ are sufficient.

The process 600 includes determining the temperature at a temperature sensor (640). Because the temperature does not change appreciably within the flow meter, the temperature at the temperature sensor may be assumed to be the same at other points within the flow meter, including the unknown location of the corrected pressure and density.

The process 600 includes determining the corrected pressure (650). This may be done, for example, by using the corrected density, the temperature, and existing algorithms for determining pressure from density and temperature.

The process 600 includes measuring the pressure at a pressure sensor (660) and determining the density at the pressure sensor (670). The density may be determined, for example, using the previously measured temperature which is assumed to be the same at the temperature sensor and the pressure sensor, and using existing algorithms for determining density from pressure and temperature.

The process 600 includes determining $k_{diff}$ using the following equation 5, by plugging in the previously determined or measured terms (680):

$$k_{diff} = \frac{2 \times (P_c - P_{ps})}{\rho_{ps} \times V_{VOR}^2} \quad (5)$$

Equation 5 is the same as equation 3 after solving for $k_{diff}$.

Figure 7:
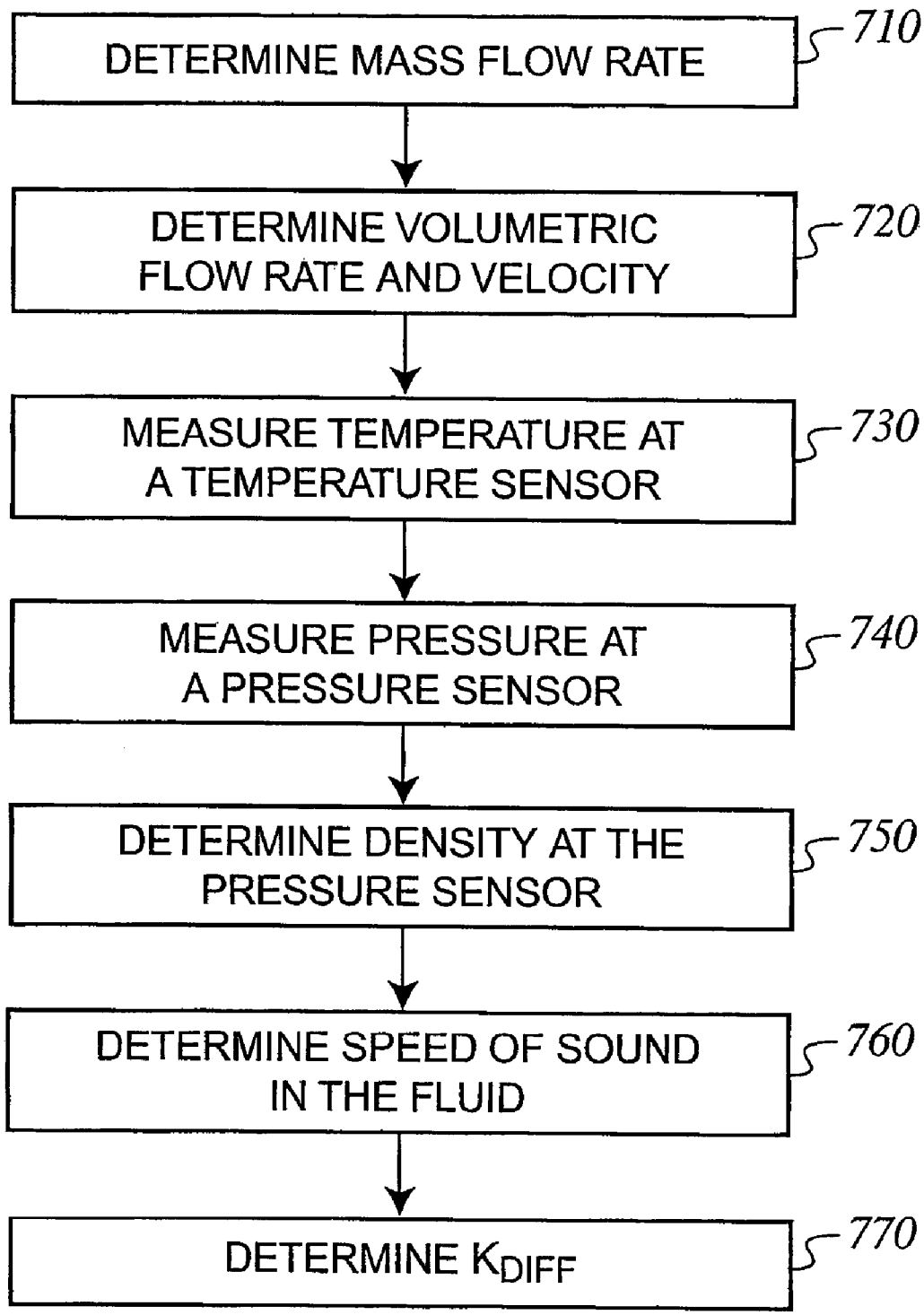
FIG. 7 shows a second calibration process to determine the term $k_{diff}$.

Referring to FIG. 7, a second calibration process 700 determines $k_{diff}$ by utilizing another relationship between density and pressure. It has been determined that the following equation 6 relates the change in density between two points in a flow meter to the change in pressure between those two points.

$$\Delta \rho = \frac{\Delta P}{c^2} \quad (6)$$

where c is the velocity of sound in the gas.

Equation 4 can be rearranged and expanded to yield equation 7 below:

$$Q_m = \rho_c \times Q_v = (\rho_{ps} + \Delta \rho) \times Q_v \quad (7)$$

Incorporating equation 6 into equation 7 yields equation 8 below:

$$Q_m = \left(\rho_{ps} + \frac{\Delta P}{c^2}\right) \times Q_v = \left(\rho_s + \frac{P_c - P_{ps}}{c^2}\right) \times Q_v \quad (8)$$

Solving equation 5 for the term $(P_c - P_{ps})$ and substituting the result into equation 8 results in equation 9 below:

$$Q_m = \rho_{ps} \times \left[1 + \frac{k_{diff}}{2} \times \left(\frac{V_{VOR}}{c}\right)^2\right] \times Q_v \quad (9)$$

Solving for $k_{diff}$ leads to the result shown in equation 10 below, $$k_{diff} = 2 \times \left(\frac{c}{V_{VOR}}\right)^2 \times \left(\frac{Q_m}{\rho_{ps} \times Q_v} - 1\right), \quad (10)$$

The process 700 includes determining the mass flow rate of the fluid through the flow meter (710), and determining the volumetric flow rate and the velocity of the fluid through the flow meter (720). These operations are analogous to operations 610 and 620, respectively.

The process 700 includes measuring the temperature at a temperature sensor (730), measuring the pressure at a pressure sensor (740), and determining the density at the pressure sensor (750). These operations are analogous to operations 640, 660, and 670, respectively.

The process 700 includes determining the speed of sound in the fluid (760). The speed is determined at the measured temperature and pressure. Calibration tests may be performed in air to take advantage of the fact that the speed of sound in air as a function of temperature and pressure is well known.

The process 700 includes determining $k_{diff}$ based on equation 10 (770). The determined value of $k_{diff}$ can then be used during operation of the flow meter to determine corrected pressure.

As discussed above, the corrected pressure is that pressure that leads to a density that can be multiplied by the measured volumetric flow rate (determined by a vortex flow meter or otherwise) to yield the correct mass flow rate. Many techniques for determining the density corresponding to the corrected pressure (and the assumed constant temperature) involve lengthy computations and iterative algorithms. Such techniques introduce delays into the real-time determination of density.

An implementation discussed below determines density, as a function of temperature and pressure, by accessing pre-computed values reflective of the density and interpolating between the accessed values. This implementation can be used, for example, to determine the density at the pressure sensor (670, 750) and to determine the corrected density during non-calibration operations.

In this implementation, the pre-computed values are stored in a table so that the values can be accessed. The stored values are not density, however, because density can vary by several orders of magnitude, which can make it difficult to use a simple interpolation algorithm between two or more points. Instead, an error term reflective of the difference between the density and a standard approximation is stored. The error term has a smaller range, allowing a simpler interpolation algorithm. Further, the error term may be scaled to a supported range to provide better precision in calculations. The stored values are computed according to the following equation 11:

TableValue=ScaleFactor*(standard density)/(approximated density) (11)

In operation, when a density is needed, the appropriate table values are accessed and interpolated to provide a TableValue corresponding to the pressure and temperature pair. To determine the density, the approximated density is calculated, multiplied by the interpolated TableValue, and divided by the known and constant ScaleFactor. Both the processes of creating one or more tables, and using those tables are now described in more detail with respect to a particular implementation.

Figure 8:
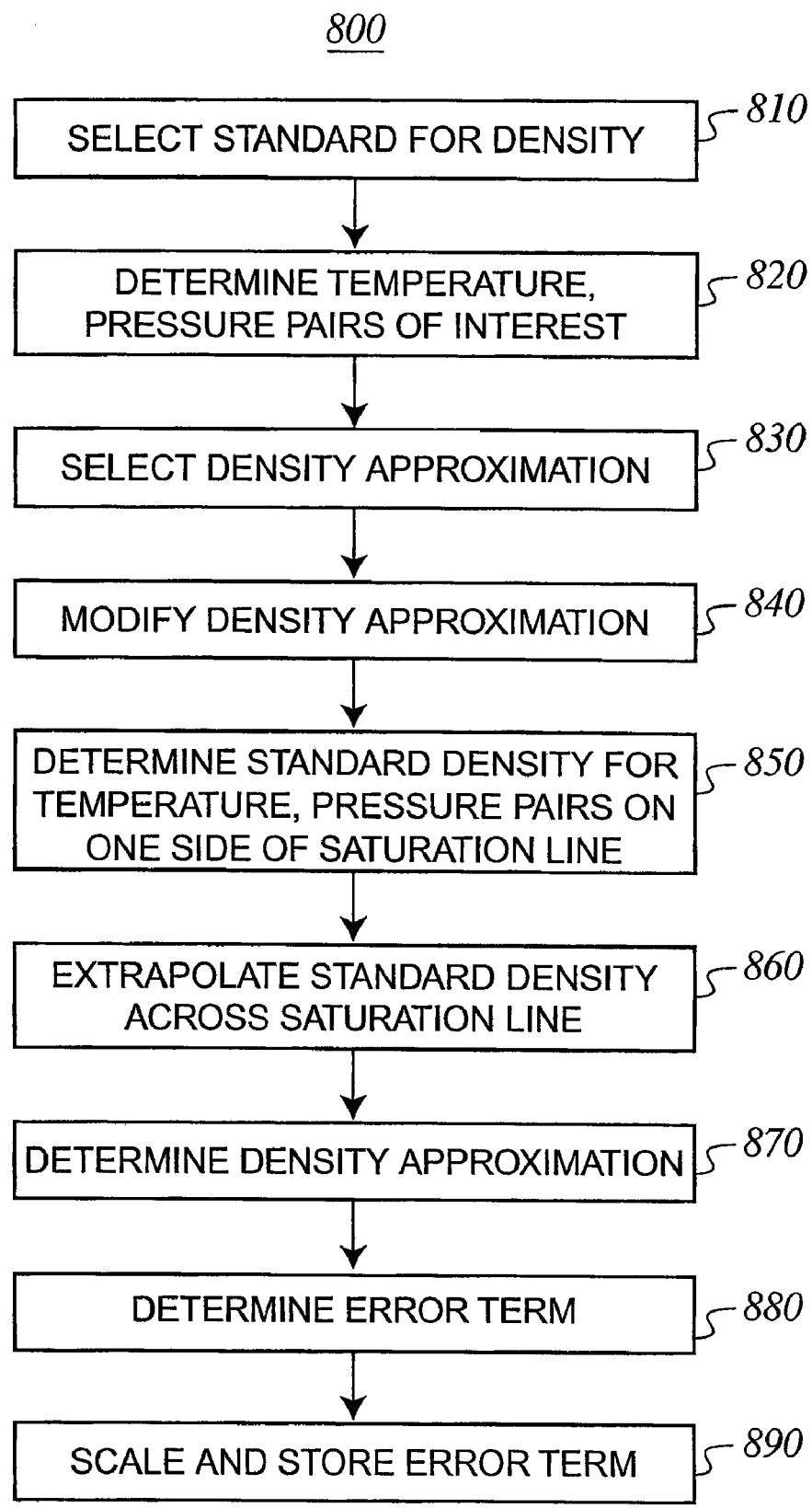
FIG. 8 shows a process for creating a table of density errors.

Referring to FIG. 8, a process 800 for creating a table includes selecting a standard for determining density values (810). An equation for density as a function of temperature and pressure can be selected from, for example, one of several available sources/standards. Examples of sources/standards include (i) the steam equation from the American Society of Mechanical Engineers ("ASME"), (ii) the America Gas Association Report No 8 for Natural Gas ("AGA8"), (iii) the America Gas Association Report No 4 for Natural Gas ("AGA4"), (iv) the America Gas Association NX-19 Gas Supercompressibility ("NX19"), and (v) *Thermodynamic Properties in SI*, by William. C. Reynolds, copyright 1979 ("Reynolds").

The process 800 includes determining temperature and pressure pairs of interest (820). This may include, for example, determining the actual pairs of interest or determining a range of pairs of interest. The temperature, pressure pairs need not be evenly spaced apart in either temperature or pressure. This allows one or more areas of greater change in the density, for example, to have pairs that are more closely spaced (higher sampling) than areas of lesser change. By spacing pairs more closely when the density is changing more rapidly, the range of the error term will be reduced and a simpler interpolation algorithm may be used.

The process 800 includes selecting a density approximation (830). In one implementation, the Virial Equation, provided by the American Institute of Chemical Engineers ("AIChE"), is used. The implementation does not simply compute the Virial Equation density approximation and store that figure in a table as the density because the Virial Equation density approximation may have up to several percent error. The Virial Equation is given by equation 12 below:

$$B(T) = a + b/T + c/T^3 + d/T^8 + e/T^9 \quad (12)$$

where,

B(T) is the molar density expressed in units of $m^3/kg*mol$,

T is the temperature in degrees Kelvin, and a-e are constant coefficients.

The AIChE provides the coefficients a-e. B(T) does not represent an approximation to the standard volumetric density, but can be converted to a standard volumetric density with the following equation 13:

$$VEDensity = (Mol. Wt.)/(UGC*T/P + B(T)) \quad (13)$$

where,

VEDensity is the density based on the Virial Equation, expressed in kg/m3,

Mol. Wt. is the molecular weight, a constant for a particular material, expressed in kg/kg*mol, UGC is the Universal Gas Constant, expressed in Joule/(g*mol*deg Kelvin), and P is the absolute pressure, expressed in PAA.

The process 800 includes modifying the density approximation (840). This operation is optional, as are various other operations even if not explicitly noted. In one implementation, the Virial Equation is modified by both using a lower order approximation of the Virial Equation and by tailoring the Virial Equation to the specific density values of interest.

It has been determined the first three terms of the Virial Equation provide a reasonable approximation to the Virial Equation while also reducing the computational requirements. Equation 14 shows this approximation:

$$Ba(T) = a + b/T + c/T^3 \quad (14)$$

where $Ba(T)$ is an approximation to $B(T)$, expressed in $m^3/kg*mol$.

Although the coefficients for the Virial Equation are provided by AIChE, a better approximation is possible in one implementation by tailoring the coefficients to the density values of interest. The coefficients can be tailored by fitting the standard density values into the form of the Virial Equation (or the form of the approximation to the Virial Equation). Solving equation 13 for $B(T)$, and substituting the standard density for the VEDensity yields equation 15 below:

$$Bvalue = (Mol. Wt./StdDensity(T,P)) - (UGC*T/P) \qquad (15)$$

A table of Bvalues can be created for various T,P pairs of interest as shown in TABLE 1 below, and the table represents the desired values of $B(T)$:

TABLE 1

| P | T | Bvalue |
|---|---|---|
| P0 | T0 | Bvalue(0)(0) |
| P0 | ... | ... |
| P0 | Tm | Bvalue(0)(m) |
| ... | ... | ... |
| ... | ... | ... |
| Pn | T0 | Bvalue(n)(0) |
| Pn | ... | ... |
| Pn | Tm | Bvalue(n)(m) |

The data can be fit to the form of the Virial Equation (or an approximation) using a least squares method, for example. The equation to be solved would take the form of equation 16 below:

$$Bvalue = a + b/T + c/(T)^3 + d/(T)^8 + e/(T)^9 \qquad (16)$$

Because the change in density is proportional to the change in $1/T$, we substitute $iT = 1/Tm$, which yields equation 17 below:

$$Bvalue = a + b*iT + c*(iT)^3 + d*(iT)^8 + e*(iT)^9 \qquad (17)$$

Solving equation 17 yields the coefficients a-e.

The process 800 includes determining the standard density for the temperature, pressure pairs of interest that are on one side of the saturation line (850). The standard density is determined, for example, using the standard selected in operation 810. To determine whether a temperature, pressure pair has crossed over the saturation line, one implementation uses a standard equation for the saturation line.

The process 800 includes extrapolating the standard density values across the saturation line for all temperature, pressure pairs of interest on the other side of the saturation line (860). An extrapolated density value is used instead of the actual density value because the density can be very non-linear at, and near, the saturation line. Extrapolating standard density values across the saturation line (for example, from gas to liquid, or from liquid to gas), and storing a related point in the table, allows the table to be interpolated for a temperature, pressure point arbitrarily close to the saturation line using the same interpolation algorithm that is used with the rest of the table. Rather than storing extrapolated density values from the other side of the saturation line, other implementations may detect when a temperature, pressure pair is close to the saturation line and then use a different technique to determine the density. Implementations may also interpolate/extrapolate needed density values from existing table points on the same side of the saturation line; however, providing one or more extrapolated points can improve the accuracy of the interpolation.

Figure 9:
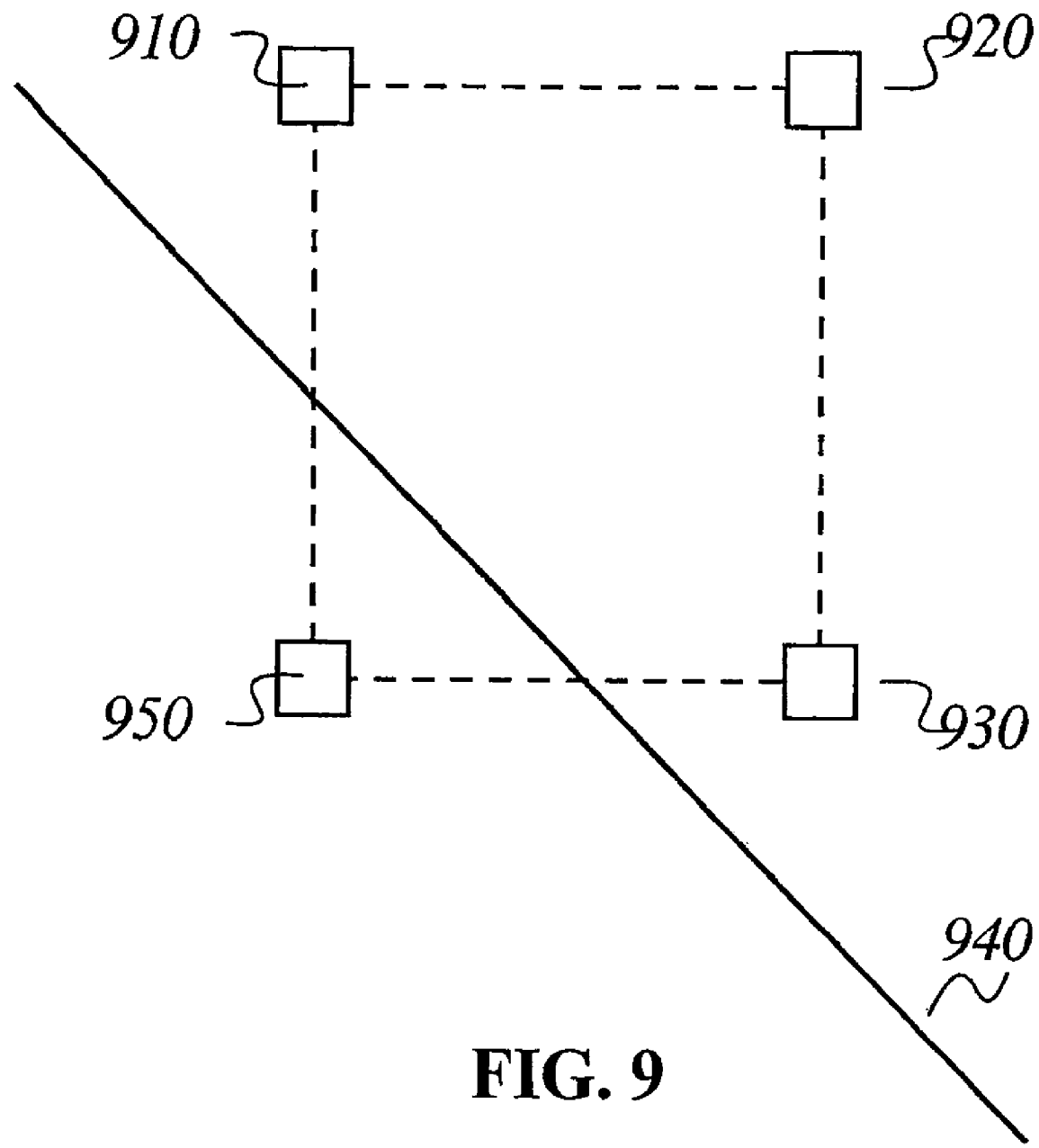
FIG. 9 shows temperature, pressure pairs on two sides of a saturation line.

Referring to FIG. 9, a graph 900 shows three temperature, pressure points 910, 920, 930 on the gas side a saturation line 940, and a temperature, pressure point 950 on the liquid side of the saturation line 940. All four points 910, 920, 930, 950 correspond to temperature, pressure pairs having a corresponding entry in a density error table.

In one implementation, extrapolated points are needed on the liquid side of the saturation line. Density values are computed for 300-400 temperature, pressure pairs near the needed point, but on the gas side of the saturation line, using a standard density algorithm. These density values are then fit to equation 18 below, which is a second-order equation that will be relatively simple to extrapolate:

$$D = c0 + c1*P + c2*P^2 + (c3 + c4*P + c5*P^2)*T + (c6 + c7*P)*T^2 \qquad (18)$$

After the coefficients c0-c7 are determined, equation 18 can be used to compute the extrapolated standard density for temperature, pressure pairs of interest.

The process 800 includes determining the density approximation for each temperature, pressure pair of interest (870). This may be done, for example, using equation 13 above for the density based on the Virial Equation. If the approximation breaks down over the saturation line, then an extrapolation may be used.

The process 800 includes determining an error term for each of the temperature, pressure points in the table (880). In one implementation, the error term is the ratio of the standard density value to the approximated density value, as indicated in equation 11 above. Other implementations may use, for example, the inverse ratio (approximated density/standard density, or a difference between the approximated density and the standard density.

The process 800 includes scaling the error term and storing the scaled error term in the table (890). The range of error terms computed may be scaled, but scaling is optional in the process 800. Scaling may provide various advantages. For example, scaling may lower the required processor time if the table can be implemented with integers and the errors are still acceptable.

If non-even spacing is used, as indicated in operation 820, one or more variable-arrays can be created to index into the density error table. In one implementation, a temperature array and a pressure array are created that store each of the temperature and pressure values represented in the density error table. TABLE 2 below shows a pressure array (columns one and two) and a temperature array (columns three and four) for such an implementation. In TABLE 2, the pressure and temperature are listed that correspond to each of the indices, Pindex and Tindex, into the density error table. For example, the density error value in the second row and second column of the density error table corresponds to a pressure of 100,000 PAA and a temperature of 315 degrees Kelvin.

TABLE 2

| Pressure (PAA) | Pindex | Temperature (K) | Tindex |
|---|---|---|---|
| 0 | 1 | 300 | 1 |
| 100,000 | 2 | 315 | 2 |
| 200,000 | 3 | 318 | 3 |
| ... | ... | ... | ... |
| 1,000,000 | N − 1 | 500 | M − 1 |
| 10,000,000 | N | 600 | M |

Other mechanisms may be used to index into the density table. Examples include arrays, tables, equations, and programs statements, such as, for example, "case" statements from C.

Figure 10:
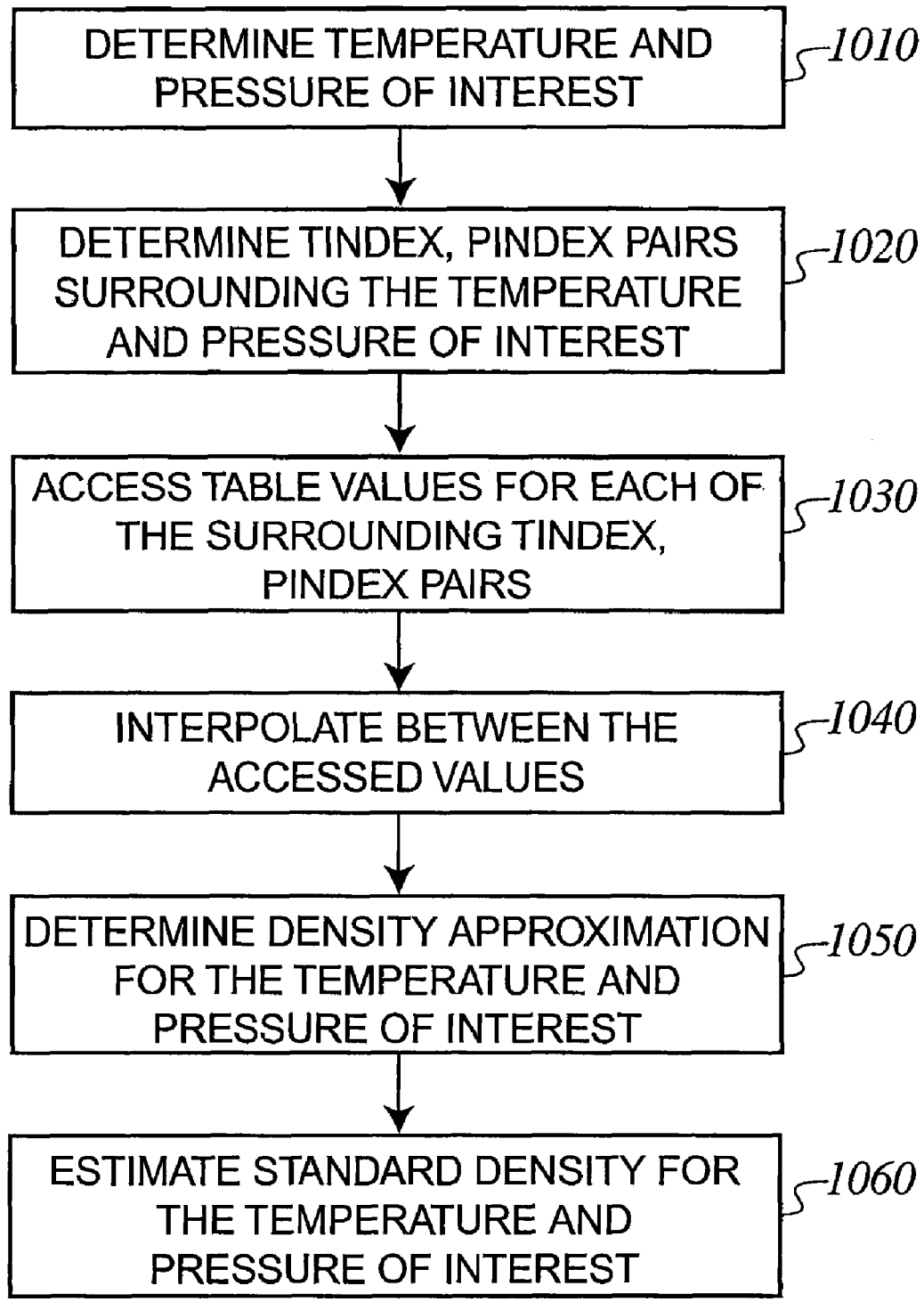
FIG. 10 shows a process for using a table created with the process of FIG. 8.

Referring to FIG. 10, a process 1000 for using a table such as that created with the process 800 includes determining the temperature and pressure for which the density is desired (1010). These values may be supplied, for example, from sensors and/or from a pressure value that has been corrected, as described earlier.

The process 1000 includes determining the Tindex, Pindex pairs surrounding the temperature and pressure of interest (1020). This may be done, for example, using a table such as TABLE 2 above. In one implementation, 2×2 linear interpolation is used and, therefore, four surrounding pairs are determined unless the temperature or the pressure is the same as that of one of the indices.

The process 1000 includes accessing table values for each of the surrounding Tindex, Pindex pairs (1030), and interpolating between these pairs (1040). TABLE 3 below shows, for one implementation, the four pairs of surrounding Tindex, Pindex pairs and the associated table values that are accessed.

TABLE 3

| Y1 (TindexStart + 1) | Tbl2 | Tbl3 |
|---|---|---|
| Y0 (TindexStart) | Tbl0 | Tbl1 |
|  | X0 (PindexStart) | X1 (PindexStart + 1) |

The four table values can be interpolated, in one implementation, by solving the following set of four equations 19.1-19.4:

$$Tbl0 = A + B*X0 + C*Y0 + D*X0*Y0 \quad (19.1)$$

$$Tbl1 = A + B*X1 + C*Y0 + D*X1*Y0 \quad (19.2)$$

$$Tbl2 = A + B*X0 + C*Y1 + D*X0*Y1 \quad (19.3)$$

$$Tbl3 = A + B*X1 + C*Y1 + D*X1*Y1 \quad (19.4)$$

where,
X0 and X1 are the pressure at the corresponding index, expressed in PAA,
Y0 and Y1 are 1/temperature at the corresponding index, expressed in 1/degrees K, and
Tbl0-Tbl3 are the table values, which are unitless.

Equations 19.1-19.4 can be solved for the coefficients A-D with the pseudo-code in TABLE 4 below:

TABLE 4

```
dX10 = X1 - X0
dY01 = Y0 - Y1
dTbl10 = Tbl1 - Tbl0
D = (tbl2 - tbl3 + dTbl10)/(dX10 * dY01)
dX0 = -D * X0
C = ((tbl0 - tbl2)/dY01) + dX0
B = dTbl10/dX10 - D * Y0
A = tbl0 - B * X0 - C * Y0 + dX0 * Y0
```

After the values for the coefficients A-D are determined by solving equations 19.1-19.4, the interpolated table value can be determined as follows in equation 20:

$$InterpolatedTblVal = A + B*X + C*Y + D*X*Y \quad (20)$$

where,
X is the pressure value of interest, expressed in PAA,
Y is the inverse of the temperature value of interest, expressed in 1/degrees K, and
InterpolatedTblVal is the interpolated value of the table, which is unitless.

The process 1000 includes determining a density approximation for the temperature and pressure of interest (1050). In one implementation, a density approximation is calculated according to equation 13, using the virial equation as described in either equation 12 or equation 14.

The process 1000 includes estimating the standard density for the temperature and pressure of interest (1060). In one implementation, the standard density is estimated according to equation 11 by solving for "standard density" and substituting "InterpolatedTblVal" for "TableValue," yielding equation 21 below:

$$Est.D = InterpolatedTblVal*(Approx. Density)/ScaleFactor \quad (21)$$

where,
Est.D is the estimate of the standard density, and
Approx. Density is the approximated density.

For temperature, pressure pairs that correspond to density error table entries, the estimate will be the same as the standard density value, assuming no precision is lost in the calculations. The term estimating is used as a subset of the term determining.

The process 1000 may be used with multiple tables. In one implementation, density tables are created for a variety of materials and for different states for each of the materials, with one table per state per material. The process 1000 is informed of the table to use by, for example, providing the process 1000 information on the material and state or providing the process 1000 an address or other pointer to the appropriate table. In this implementation, the process 1000 uses the same interpolation process or technique and the same equation for determining approximated density for each of the states and materials. It is not necessary, however, in this implementation, to use the same standard for each of the states and materials. Other implementations of the process 1000 use different interpolation processes or techniques and/or different equations for approximated density for the various supported states and materials, and provide information to the process 1000 indicating which process or technique and/or equations to use.

The processes 800 and 1000 can be combined in an implementation that produces density determinations within 0.1% of the standard density value, while at the same time requiring relatively minimal calculations by the end device. This may be advantageous for end devices, such as, for example, vortex flow meters, other metering devices, and other devices used to process data. Many end devices include controllers having limited random access memory ("RAM") and clock rates. Controllers include, for example, processors, controller chips and chip sets, application specific integrated circuits ("ASICS"), programmable logic devices ("PLDs"), digital signal processors ("DSPs"), and other devices capable of executing instructions.

Additional Variations

Referring again to FIG. 2, the current controller 240 may be implemented, at least in part, using a set point voltage and feedback control. The switch 241 may be implemented, at least in part, using a set point comparator controlling a transistor switch. The voltage dividers 246, 247 may be implemented, at least in part, using a switched capacitor charge transfer circuit. The voltage may be shunt regulated at $V_0$ and $V_0/2$, at least in part, using a set point comparator and a load dumping switch.

The processes and systems described above for determining and using corrected pressure and/or the corrected density can be used in a variety of applications that require density, including, for example, tank level calculations, steam quality determinations, and energy content determinations.

The components and operations described in the various implementations above may generally be interchanged, supplemented, or omitted. For example, a circuit component such as, for example, a resistor, a capacitor, an inductor, a transformer, an isolator, an operational amplifier, or a filter may be desired in one or more locations of an implementation. The terms "coupled" and "injected," and their cognates, are understood to allow for other components to be disposed between two coupled components or between a switch and an injection point, for example.

As indicated earlier, the transmitter may communicate over other communication lines, including, for example, 2-wire, 3-wire, cable, and free space. The implementations disclosed may be used with devices, such as, for example, transmitters, that do not regulate a received current amplitude. For example, a device may receive a variable current from a supply and may use the power management concepts disclosed herein to reduce the voltage required by the device when a high current is being received. The current regulation, control, or varying, may be done by another device, such as, for example, a control room or a supply. Additionally, the varying current need not encode information. The disclosed implementations for data processing may be used with a variety of communication systems including, but not limited to, a 4-20 mA system. Other communication systems, standards, techniques, and protocols, including, for example, Foundation fieldbus by the Fieldbus Foundation of Austin, Tex., the HART standard, and other digital, analog, or hybrid analog/digital techniques. The various concepts disclosed herein can be used independently and need not be combined.

Various of the processes, algorithms, and techniques disclosed may be implemented in instructions that can be stored on a storage medium, such as, for example, a floppy diskette, a compact diskette, a hard disk, random access memory ("RAM"), or read only memory ("ROM"). A storage medium may be included in a device, such as, for example, a controller.

A number of implementations have been described. Nevertheless, it will be understood that various modifications may be made. Accordingly, other implementations are within the scope of the following claims.

What is claimed is:

1. A computer program product tangibly embodied in a non-transitory machine-readable storage medium, wherein the computer program product comprises instructions that, when read by a machine, operate to cause data processing apparatus to:
   determine a standard density value for each of a plurality of input pairs, each input pair including a temperature value and a pressure value;
   determine a density approximation for each input pair using a virial equation expressed by:

$$B(T) = a + \frac{b}{T} + \frac{c}{T^3} + \frac{d}{T^8} + \frac{e}{T^9},$$

wherein B(T) represents molar density expressed in units of $m^3/kg \cdot mol$, T represents temperature in degrees Kelvin, and a to e are coefficients tailored to the standard density value of the each input pair;
   determine a density error ratio for each input pair based on the standard density value and the density approximation of the each input pair;
   scale the density error ratios; and
   store the scaled density error ratios in a table for later retrieval.

2. A computer program product tangibly embodied in a non-transitory machine-readable storage medium, wherein the computer program product comprises instructions that, when read by a machine, operate to cause data processing apparatus to:
   determine a standard density value for an input pair, the input pair including a temperature value and a pressure value;
   determine a density approximation of the input pair using the temperature value and the pressure value;
   determine a density error for the input pair based on the standard density value and the density approximation of the input pair; and
   store the density error,
      wherein the instructions that, when read by the machine, operate to cause the data processing apparatus to determine the density approximation by implementing a virial equation expressed by:

$$B(T) = a + \frac{b}{T} + \frac{c}{T^3} + \frac{d}{T^8} + \frac{e}{T^9},$$

wherein B(T) represents molar density expressed in units of $m^3/kg \cdot mol$, T represents temperature in degrees Kelvin, and a to e are coefficients tailored to the standard density value of the each input pair.

3. The computer program product of claim 2, further comprising instructions that, when read by the machine, operate to cause the data processing apparatus to scale the density error.

4. The computer program product of claim 2, wherein the instructions that, when read by the machine, operate to cause the data processing apparatus to determine the density approximation implementing an approximation equation having three or less terms.

5. The computer program product of claim 2, wherein the density error comprises a density error ratio.

6. The computer program product of claim 2, further comprising instructions that, when read by the machine, operate to cause the data processing apparatus to:
   determine a second standard density value for a second input pair, the second input pair including a temperature value and a pressure value;
   determine a second density approximation of the second input pair using the temperature value and the pressure value included in the second input pair;
   determine a second density error for the second input pair based on the second standard density value and the second density approximation; and
   store the second density error.

7. The computer program product of claim 6, further comprising instructions that, when read by the machine, operate to cause the data processing apparatus to solve for a standard density value for third input pair, via interpolation.

8. The computer program product of claim 6, wherein at least one of the pressure value included in the input pair and the pressure value included in the second input pair are not equally spaced in pressure, and the temperature value included in the input pair and the second temperature value included in the second input pair are not equally spaced in temperature.

9. The computer program product of claim 6, wherein the instructions that, when read by the machine, operate to cause the data processing apparatus to determine the second standard density value comprise instructions that cause the data processing apparatus to extrapolate from other standard density values on a first phase side of a saturation line to determine the second standard density value, wherein the second standard density value is disposed on a second phase side of the saturation line.

10. The computer program product of claim 6, wherein the instructions that, when read by the machine, operate to cause the data processing apparatus to determine the second density approximation implementing an approximation equation tailored to a plurality of standard density values including the second standard density value.

11. The computer program product of claim 6, wherein the instructions that, when read by the machine, operate to cause the data processing apparatus to determine the second density approximation implement a virial equation having a plurality of coefficients tailored to a plurality of standard density values including the second standard density values.

12. A computer-implemented method of generating a density error table, comprising:
determining a standard density value for an input pair, the input pair including a temperature value and a pressure value;
determining a density approximation of the input pair using the temperature value and the pressure value;
determining a density error for the input pair based on the standard density value and the density approximation of the input pair; and
storing the density error,
wherein determining the density approximation comprises implementing a virial equation and the virial equation expressed by:

$$B(T) = a + \frac{b}{T} + \frac{c}{T^3} + \frac{d}{T^8} + \frac{e}{T^9},$$

wherein B(T) represents molar density expressed in units of $m^3/kg \cdot mol$, T represents temperature in degrees Kelvin, and a to e are coefficients tailored to the standard density value of the each input pair.

13. The method of claim 12, further comprising scaling the density error.

14. The method of claim 12, wherein the density approximation is determined using a virial equation tailored to the standard density values.

15. The method of claim 12, wherein determining the density error comprises determining a ratio based on the standard density value and the density.

16. A device, comprising:
a processor configured to:
determine a standard density value for an input pair, the input pair including a temperature value and a pressure value,
determine a density approximation of the input pair using the temperature value and the pressure value, and
determine a density error for the input pair based on the standard density value and the density approximation of the input pair,
wherein the processor is configured to determine the density approximation by implementing a virial equation and the virial equation expressed by:

$$B(T) = a + \frac{b}{T} + \frac{c}{T^3} + \frac{d}{T^8} + \frac{e}{T^9},$$

wherein B(T) represents molar density expressed in units of $m^3/kg \cdot mol$, T represents temperature in degrees Kelvin, and a to e are coefficients tailored to the standard density value of the each input pair; and
a storage medium configured to store the density error.

17. The device of claim 16, wherein the processor is further configured determine the density approximation implementing a virial equation having a plurality of coefficients tailored to the standard density value.

18. The device of claim 16, wherein the density error comprises a ratio based on the standard density value and the density approximation.

19. A computer program product tangibly embodied in a non-transitory machine-readable storage medium, wherein the computer program product comprises instructions that, when read by a machine, operate to cause data processing apparatus to:
determine a standard density value for an input pair, the input pair including a temperature value and a pressure value;
determine a density approximation for the input pair by implementing a virial equation expressed by:

$$B(T) = a + \frac{b}{T} + \frac{c}{T^3} + \frac{d}{T^8} + \frac{e}{T^9},$$

wherein B(T) represents molar density expressed in units of $m^3/kg \cdot mol$, T represents temperature in degrees Kelvin, and a to e are coefficients tailored to the standard density value of the each input pair;
determine a density error for the input pair based on the standard density value and the density approximation of the input pair; and
store the density error for later retrieval.

20. A computer-implemented method of generating a density error table, comprising:
determining a standard density value for an input pair, the input pair including a temperature value and a pressure value;
determining a density approximation for the input pair by implementing a virial equation expressed by:

$$B(T) = a + \frac{b}{T} + \frac{c}{T^3} + \frac{d}{T^8} + \frac{e}{T^9},$$

wherein B(T) represents molar density expressed in units of $m^3/kg \cdot mol$, T represents temperature in degrees Kelvin, and a to e are coefficients tailored to the standard density value of the each input pair;

determining a density error for the input pair based on the standard density value and the density approximation of the input pair; and storing the density error for later retrieval.

21. A device comprising:

a processor configured to:

determine a standard density value for an input pair, the input pair including a temperature value and a pressure value;

determine a density approximation for the input pair by implementing a virial equation expressed by:

$$B(T) = a + \frac{b}{T} + \frac{c}{T^3} + \frac{d}{T^8} + \frac{e}{T^9},$$

wherein B(T) represents molar density expressed in units of $m^3$/kg·mol, T represents temperature in degrees Kelvin, and a to e are coefficients tailored to the standard density value of the each input pair;

determine a density error for the input pair based on the standard density value and the density approximation of the input pair; and a storage medium configured to store the density error for later retrieval.

* * * * *